United States Patent
Bekker et al.

(10) Patent No.: US 11,166,908 B2
(45) Date of Patent: Nov. 9, 2021

(54) COMPOSITION FOR PREPARING AN ANTI-TUMOUR AGENT AND A METHOD FOR PREPARING AN ANTI-TUMOUR AGENT ON THE BASIS OF SAME

(71) Applicant: German Petrovich Bekker, Moscow (RU)

(72) Inventors: German Petrovich Bekker, Moscow (RU); Boris Alekseevich Nikonov, St. Petersburg (RU)

(73) Assignee: German Petrovich Bekker, Moscow (RU)

( * ) Notice: Subject to any disclaimer, the term of this patent is extended or adjusted under 35 U.S.C. 154(b) by 0 days.

(21) Appl. No.: 16/473,423

(22) PCT Filed: Aug. 29, 2017

(86) PCT No.: PCT/RU2017/000624
§ 371 (c)(1),
(2) Date: Jun. 25, 2019

(87) PCT Pub. No.: WO2018/124933
PCT Pub. Date: Jul. 5, 2018

(65) Prior Publication Data
US 2020/0306179 A1    Oct. 1, 2020

(30) Foreign Application Priority Data
Dec. 29, 2016   (RU) .............. RU2016152267

(51) Int. Cl.
*A61K 9/00*      (2006.01)
*A61K 33/243*    (2019.01)
*A61K 38/10*     (2006.01)
*A61K 9/08*      (2006.01)

(52) U.S. Cl.
CPC .......... *A61K 9/0019* (2013.01); *A61K 33/243* (2019.01); *A61K 38/10* (2013.01); *A61K 9/08* (2013.01)

(58) Field of Classification Search
CPC ..... A61K 33/243; A61K 38/10; A61K 9/0019
See application file for complete search history.

(56) References Cited

U.S. PATENT DOCUMENTS

| | | | | |
|---|---|---|---|---|
| 4,310,515 A | * | 1/1982 | Granatek | A61K 33/24 424/649 |
| 2004/0138137 A1 | * | 7/2004 | Kim | A61P 35/00 435/5 |

FOREIGN PATENT DOCUMENTS

| | | |
|---|---|---|
| RU | 2128042 | 3/1999 |
| RU | 2145234 | 2/2000 |
| RU | 2172322 | 8/2001 |
| RU | 2470031 | 12/2012 |
| RU | 2482366 | 5/2013 |
| SU | 1701323 | 12/1991 |
| WO | WO2016036273 | 3/2016 |

* cited by examiner

*Primary Examiner* — Mark V Stevens
(74) *Attorney, Agent, or Firm* — Defillo & Associates, Inc.; Evelyn A. Defillo

(57) ABSTRACT

The invention relates to pharmacology and to a composition for making an antitumor agent in the form of a solution for injection. The composition contains alloferon at a concentration of 0.05 to 0.1% wt, cis-diamminedichloridoplatinum at a concentration of 0.01 to 0.05% wt, and water. The composition of the present invention features antitumor activity and hypotoxicity. 1 Figure, 3 Tables, 5 examples.

1 Claim, 1 Drawing Sheet

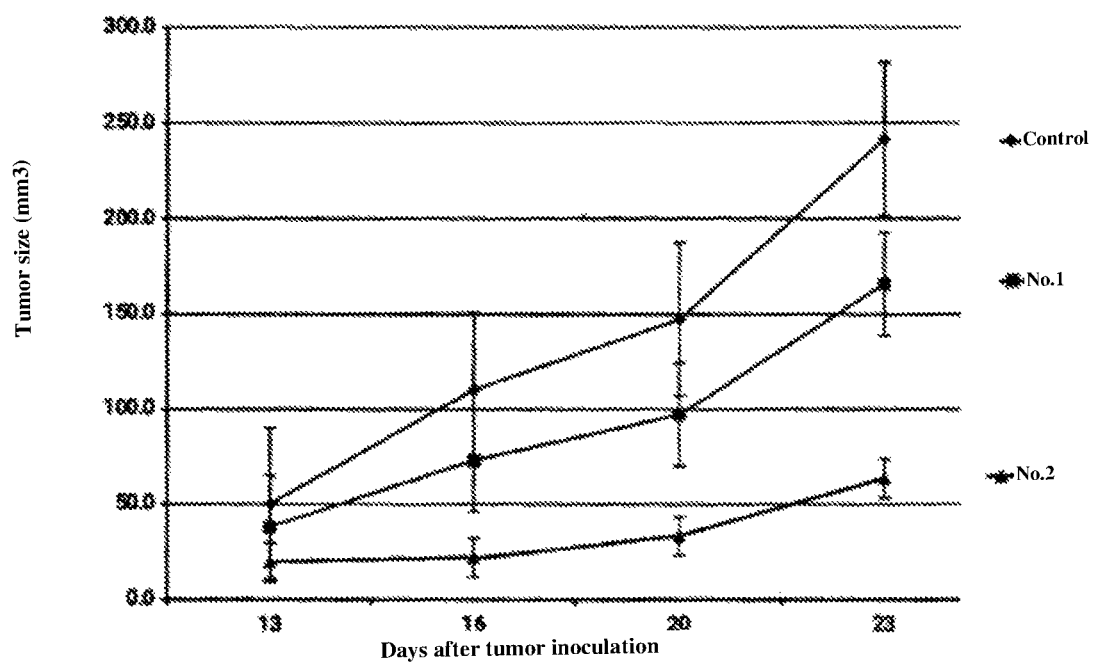

COMPOSITION FOR PREPARING AN ANTI-TUMOUR AGENT AND A METHOD FOR PREPARING AN ANTI-TUMOUR AGENT ON THE BASIS OF SAME

CROSS REFERENCE TO RELATED APPLICATION

This application is a national stage entry of PCT/RU2017/000624 filed Aug. 29, 2017, under the International Convention and claiming priority over Russian Patent Application No. RU2016152267 filed Dec. 29, 2016.

FIELD OF THE INVENTION

The invention relates to pharmacology and to a composition for making an antitumor agent, which is a complex of divalent platinum salts and the alloferon peptide, and to pharmaceutical compositions comprising said complexes. It may be used to produce oncology products.

BACKGROUND OF THE INVENTION

Search for new antitumor active products is one of the main focuses of modern biophysics, molecular biology, chemistry, and medicine. Products based on metal complexes of which the platinum-based complexes are the best known have a special place among the known antitumor active products.

Application of platinum complexes in anticancer chemotherapy is well known to those skilled in the art. However, divalent platinum, i.e. platinum(II), is primarily used to this end. Platinum-containing products typically used in cancer treatment include cisplatin, carboplatin, oxaliplatin, etc. However, such compounds do not prove to be useful in treating any types of tumors; moreover, cancer cells of certain types may exhibit resistance to such drugs. One major disadvantage of said platinum-containing products is that they are characterized by high neurotoxicity, ototoxicity, nephrotoxicity, myelosuppression, and produce a large number of adverse side effects.

Platinum products feature a broad spectrum of antitumor activity. Cis-diamminedichloridoplatinum (DDP) is active against tumors of various origins: spontaneous, inoculated, virus-induced and chemical carcinogen-induced tumors. The main disadvantage of DDP is its high toxicity resulting in renal, medullary and gastrointestinal disorders (Biologicheskiye aspekty koordinatsionnoy khimii ('Biological Aspects of Coordination Chemistry'), under the editorship of K. B. Yatsimirskyi. Kyiv. Naukova dumka. 1979, pp. 149-180).

Antitumor activity of platinum(II) complex compounds is attributed to the formation of strong bods with the nitrogenous bases (mainly with guanine) of DNA resulting in tumor cell apoptosis. It is known that by far not the entire amount of administered product is received in the cells. The majority of it is renally excreted from the blood stream, primarily intact or in the form of tetramine complexes. For this very reason, the excretory system is that most affected by the platinum drugs' side effects.

The DDP product (marketed under the trade name Cisplatin) is used in rather high doses, thus increasing the likelihood of adverse effects related to platinum-based products' toxicity.

Studies of various platinum complexes in animals and clinical trials of DDP and some of its analogues have revealed a variety of the platinum complexes' biological properties: antitumor activity and side effect. It was demonstrated that minor changes in the molecular structure of a complex may cause dramatic changes in its biological activity. The connection existing between the structure of a complex compound and its antitumor activity encourages searching for platinum-containing products that are highly active and low-toxic.

Just after the (DDP's) antitumor effect was discovered, many laboratories worldwide undertook investigations of its structural analogues. Notwithstanding the fact that molecular mechanisms of their effect on cellular structures are still far from understood, some success has been achieved: solubility has been improved, toxicity has been reduced, cellular permeability has been improved, etc. Unfortunately, very few of the discovered drugs exceeded DDP in therapeutic index (activity to toxicity ratio).

Two methods are mainly used in developing new DDP-based antitumor products: 1. Chemical modification of a molecule by introducing various substituents into it (the substituents are typically introduced to substitute one or two chlorine atoms), 2. Complexing DDP with another compound, including with a compound having its own biological activity.

By using the first method, antitumor drugs that have come into clinical practice, such as: Carboplatin (cis-Diammine (1.1-cyclobutanedicarboxylato)platinum), Oxaliplatin ([(1R,2R)-1,2-cyclohexanediamine-N,N'][oxalato(2)-O,O'] platinum), have been developed.

By introducing a pyridine ring into a DDP molecule, the Pyriplatin product has been created. By introducing large-size pyridine rings into DDP, Stephen J. Lippard et al. produced the Phenantriplatin product which, in studies on several cells, demonstrated an efficiency superior to that of Cisplatin.

By condensing Cisplatin with bile acids, Enzo Bartoli, Beniamino Palmieri, and Alessandro Medici (Patent WO/2003/095470, Platinum complexes having antitumor activity) have produced a drug having lower toxicity and effective against testicular and ovarian tumors.

A writing group has developed the S-malatoammine (cyclo-pentylamine)platinum (II) (Patent RU 2128042, Antitumor Agent, Cheltsov-Bebutov, P. A. et al.) that was found to be effective against several tumors resistant to Cisplatin. Platinum is known for its tendency to form coordination complex compounds. Accordingly, another method for creating platinum-containing antitumor products is to fix platinum contained therein with various ligands to form complexes. The ligands may be of various natures: either of low or high molecular weight, inert or bioactive compounds.

Described are complexes of platinum with humic acids: RF Patents 2182482, Sposob polucheniya antirakovogo sredstva ('Method for Producing an Anticancer Agent') and RF 2178702, Antirakovoye sredstvo (Anticancer Agent) by Trofimov, V. A.; Shipov, V. P.; Pigarev, E. S., Popov, A. I.; Ivanov, V. N., and RF Patent No. 2368379, Protivoopukholevoye sredstvo ('Antitumor Agent') by Shipov, V. P., Pigarev, E. S., Fedoros, E. I., Trofimova, N. P.

Platinum compounds employed by the inventors under above patents include Cisplatin, potassium tetrachloroplatinate and other platinum compounds, while using ammonium salts of lignohumic acids as the humic substances. The invention allows reducing the product toxicity while improving its cancer treatment efficiency.

It should also be noted that humic acids used as ligands have their own bioactivities: antioxidant, anti-inflammatory, antiviral and immunomodulatory.

According to known patent SU 1813089 A3, granted to Volchenkova, I. I., Maidanevich, N. N., Budarin, L. I., Shalimov, S. A., Trokhimenko, E. P., Keisevich, L. V., Sposob polucheniya soedineniya platiny (II) s DNK, obladayushchego protivoopukholevoy aktivnostiyu ('Method for Producing a Compound of Platinum(II) with Antitumor-Active DNA'), an aqueous solution containing DNA and sodium chloride is mixed with aqueous solution of DDP.

The method allows producing an agent featuring both high antitumor activity and apparent immunomodulatory effect. This work is further developed in Patent WO 2010074662 A1, O. S. Sokyrko et al., Protivoopukholevoye sredstvo, sposob ego polucheniya i sposob ego stabilizatsii ('Antitumor Agent, Method for Producing Thereof, and Method for Stabilization Thereof').

In a work by Ekimova, A. A., Alekseeva, G. M., Karavayeva, A. V., Kompleksnye soedineniya platiny s dipeptidami: biologicheskaya aktivnost' ('Complex Compounds of Platinum and Dipeptides: Bioactivity'), Farmatsia, 2014, Issue 6, p. 52-54, binuclear complexes comprised of cis-diamminedichloridoplatinum and dipeptides, such as D,L-alanyl-D,L-alanine (Ala-Ala), D,L-alanyl-glycine (Ala-Gly) D,L-alanyl-L-leucine (Ala-Leu), D,L-alanyl-L-norleucine (Ala-nLeu), are produced and described. Introduction of the dipeptides into the platinum coordination sphere allows changing the spectrum of antitumor effect through targeted delivery of the compound to a tumor cell and reducing health toxicity.

Along with the cytostatic agents that include the above platinum-based products, recombinant proteins from the interferon groups are also used in cancer treatment as antitumor immunity activators and tumor cell proliferation inhibitors. The interferons are used to treat multiple myeloma (Zee et al., J. Clin. Oncol., 1998, 16,8, p. 2834-2839), Hodgkin disease (Aviles et al. Leuk. Lymphoma, 1998, 30, 5-6, p. 651-656), myeloid leukemia (Gilbert, Cancer, 1998, 83, 6, p. 1205-13). To the same end, interferon inducing agents, such as Neovir, Cycloferon, etc., are used in cancer therapy.

Alloferon, an oligopeptide with a high antiviral activity, also falls under the category of interferon inducing agents.

'Allokin-alfa, lyophilisate for solution for subcutaneous injection, 1 mg' (P N002829/01), an antiviral medication has been produced on the basis of Alloferon. Allokin-alfa is effective in treating patients with chronic papillomavirus infection induced by carcinogenic human papillomaviruses; as part of combination therapy in the treatment of chronic Type 1 and 2 herpes recidivicus; as part of combination therapy in the treatment of moderate (icteric) acute Hepatitis B. As is known, the papillomaviruses and herpesviruses are carcinogenic. There is evidence that alloferons have antitumor properties based on activation of antitumor immunity mechanisms, i.e. interferons and natural killer cells (Chernysh et al., Proceedings of National Academy of Science, 2002, 99, p. 12628-12632). High complexing activity is a peculiarity of the alloferon family peptides. Complexes of alloferon-1 and its analogues with a large number of transition metals, including copper (M. Kuczer and other. J. Inorganic Biochemistry, 111, 2012, 40-49), nickel, etc., have been studied. It is also known (M. Kuczer and other, Inorganic Chemistry, 2013, 52, 5951-5961) that such complexes may be bioactive. As is shown in Patent RU 2470031, granted to Kiselev, O. I., Ershov, F. I., Biologicheski aktivnye peptidnye kompleksy ('Bioactive Peptide Complexes'), the level of interferon alfa induction produced by an alloferon complex is substantially higher than that established for alloferon and cycloferon.

The closest analogous solution is 'ALLOFERONS—IMMUNOMODULATORY PEPTIDES' (Patent RU 2172322, published: 20 Aug. 2001), describing new compounds with a general formula I: X1-His-Gly-X2-His-Gly-Val-X3 or their pharmaceutically acceptable salts, or ethers, or amides, where X1 is absent or contains at least 1 amino acid, X2 contains at least 1 amino acid or is a peptide link; X3 is absent or contains at least 1 amino acid, wherein said amino acids are selected from the following groups: aliphatic, aromatic or heterocyclic. The compounds stimulate the antiviral, antimicrobial and antitumor activities of the human immune system.

SUMMARY OF THE INVENTION

It is an object of the present invention to provide a composition for making an antitumor product that would combine antitumor efficiency of platinum-based compounds with that of the substances with interferon-inducing activity. Such combination may allow reducing the concentration of platinum, thus providing for reduced toxicity of the product.

The technical result of the invention is the possibility to produce, on the basis of the composition, various types of products for injection or a lyophilisate having both antitumor efficiency and hypotoxicity.

Said technical result is accomplished by providing a composition for making an antitumor agent in the form of a solution for injection or a lyophilisate, containing alloferon, characterized in that a complex compound of divalent platinum with alloferon oligopeptide is used as an active ingredient. Preferably, cis-diamminedichloridoplatinum is used as a platinum salt.

A method for making an antitumor agent on the basis of the above composition, characterized in that alloferon is gradually added to a cisplatin solution with the 0.05% concentration, the resulting solution is stirred during 15 minutes, then sterilized by filtering it through a filter with the pore size of 0.2 micrometer, and then ampouled.

Preferably, a solution is formed having a DDP concentration of 0.01 to 0.05% and an alloferon concentration of 0.05 to 0.1%.

BRIEF DESCRIPTION OF THE DRAWINGS

FIG. 1 shows the growth dynamics of an inoculated Ehrlich's carcinoma in white mice under treatment with the chemical products. As such, Products No. 1 (Cisplatin) and No. 2 exhibit antitumor properties. The product based on Composition No. 2, where a complex compound of divalent platinum with alloferon oligopeptide is used as an active ingredient, was found to be substantially (three times) more efficient than Cisplatin.

DETAILED DESCRIPTION OF THE INVENTION

Known is a family of cytokine-like peptides, i.e. alloferons, having a high antiviral activity (RU 2172322, Chernysh, S. I., Kim Su In, Bekker, G. P., Makhaldiani, N. B., Hoffmann, J., Bulet, P., Alloferony—immunomoduliruyushchie peptidy ('Alloferons—Immunomodulatory Peptides')). Alloferons act by inducing endogenous interferon production and by activating the natural killer cell system.

It is known from general chemistry that platinum has a strong tendency to form complex compounds.

The above object is accomplished by providing an antitumor medicinal product whose active principle is a complex compound of divalent platinum and alloferon peptide.

It has hypotoxicity and higher efficiency due to a combination of the antitumor properties of both platinum(II) salts and alloferons.

The present product may be either a solution for injection, or a lyophilisate.

The following examples of making various products on the basis of the claimed composition prove that the invention object may be accomplished.

Example 1

ALF : DDP Mole Ratio is 1:1.

Dry cis-diamminedichloridoplatinum in the amount of 5 mg is added to a beaker containing 10 ml of 0.9% sodium chloride solution. The solution is stirred until the salt is fully dissolved. Alloferon in the amount of 10 mg is then added to the solution. The solution is stirred during 15 minutes, then sterilized by filtering it through a filter with the pore size of 0.2 micrometer, then dispensed into ampoules in the amount of 2 ml each, and the ampoules are vacuum-sealed. The resulting solution has the DDP concentration of 0.5 mg/ml (0.05%) and the alloferon concentration of 1.0 mg/ml (0.10%).

Example 2

ALF: DDP Mole Ratio is 1:2.

Dry cis-diamminedichloridoplatinum in the amount of 5 mg is added to a beaker containing 10 ml of 0.9% sodium chloride solution. The solution is stirred until the salt is fully dissolved. Alloferon in the amount of 5 mg is then added to the solution. The solution is stirred during 15 minutes, then sterilized by filtering it through a filter with the pore size of 0.2 micrometer, then dispensed into ampoules in the amount of 2 ml each, and the ampoules are vacuum-sealed. The resulting solution has the DDP concentration of 0.5 mg/ml (0.05%) and the alloferon concentration of 0.5 mg/ml (0.05%).

Example 3

ALF: DDP Mole Ratio is 1:1.

Dry cis-diamminedichloridoplatinum in the amount of 5 mg is added to a beaker containing 10 ml of 0.9% sodium chloride solution. The solution is stirred until the salt is fully dissolved. Then mannitol in the amount of 40 mg and alloferon in the amount of 10 mg are sequentially added to the solution. The solution is stirred during 15 minutes, then sterilized by filtering it through a filter with the pore size of 0.2 micrometer, then dispensed into Fl-5 or 4D vials in the amount of 2 ml each. The vials are placed into a freeze dryer chamber and dried under standard conditions. Upon completion of the process, the vials are closed with stoppers and sealed with aluminum caps.

The resulting solution has the DDP concentration of 0.5 mg/ml (0.05%) and the alloferon concentration of 1.0 mg/ml (0.10%).

Example 4

ALF: DDP Mole Ratio is 1:2.

Dry cis-diamminedichloridoplatinum in the amount of 5 mg is added to a beaker containing 10 ml of 0.9% sodium chloride solution. The solution is stirred until the salt is fully dissolved. Then mannitol in the amount of 40 mg and alloferon in the amount of 5 mg are sequentially added to the solution. Further actions are as per Example 3. The resulting solution has the DDP concentration of 0.5 mg/ml (0.05%) and the alloferon concentration of 0.5 mg/ml (0.05%).

Example 5. Antitumor Activity Assay

Efficiency of the present invention has been demonstrated on an example product produced on the basis of Cisplatin-Teva, a marketed drug containing 0.5 mg/ml of platinum.

Three materials have been used in a comparative study:

Placebo (0.9% sodium chloride solution)

Reference product Cisplatin-Teva (Product 1)

The product described in Example 1 (Product 2).

Antitumor activity was tested on an inoculated solid Ehrlich's tumor model. The mouse strain of the solid Ehrlich's cancer to be inoculated was obtained from the Federal Public Institution—Petrov Scientific Research Institute of Oncology's bank of strains.

Outbred mice, both males and females, weighing 18 to 20 g were used in the study. The animals were kept under natural lighting conditions with free access to standard feeding stuff and water. The tumor was inoculated subcutaneously in the amount of $10^7$ cells of the 0.2 ml volume. The animals were randomly grouped. Three groups were formed to carry out the experiment:

Group 1 (n=10). The animals were treated with physiological saline (placebo),

Group 2 (n=9). The animals were treated with Product No. 1.

Group 3 (n=9). The animals were treated with Product No. 2.

Tumor node length and width were measured on the $13^{th}$, $16^{th}$, $22^{nd}$ and $25^{th}$ days of the experiment. Tumor volume was calculated from the formula:

$$V = \frac{a \cdot b^2}{2}$$

where a is the larger and b is the smaller linear size of a node. The products and the placebo were administered subcutaneously in the tumor cell injection area on the $3^{rd}$, $6^{th}$, $9^{th}$, $13^{th}$, $16^{th}$ and $20^{th}$ days after the inoculation in the amount of 0.2 ml for each mouse.

Antitumor activity of the agents under study was evaluated by comparing the tumor growth dynamics using the methods adopted in experimental oncology (Metodicheskiye rekomendatsii po doklinicheskomu izucheniyu sredstv, obladayushchikh sposobnostyu ingibirovat' protsess metastazirovaniya i povyshat' effektivnost tsitostaticheskoy terapii zlokachestvennykh opukholei ('Guidelines for Preclinical Study of Agents Capable of Inhibiting Metastasis and Enhancing Efficiency of Cytostatic Treatment of Malignant Tumors')/Under the editorship of E. D. Goldberg, A. B. Syrkin. M., 1992).

Data obtained from the studies of tumor sizes in the white mice are shown in Tables 1, 2 and 3 below, and in the Fig.

TABLE 1

Tumor (Ehrlich's Carcinoma) Growth Dynamics in White Mice (Placebo Group)

| Animal No. | 13th day | | | 16th day | | | 20th day | | | 23rd day | | |
|---|---|---|---|---|---|---|---|---|---|---|---|---|
| | a | b | V, mm³ | a | b | V, mm³ | a | b | V, mm³ | a | b | V, mm³ |
| 1 | 8 | 4 | 64 | 20 | 17 | 2890 | 20 | 16 | 2560 | 21 | 20 | 4200 |
| 2 | 12 | 10 | 600 | 18 | 15 | 2025 | 17 | 17 | 2456.5 | 9 | 7 | 220.5 |
| 3 | 18 | 15 | 2025 | 12 | 7 | 294 | 0 | 0 | 0 | 0 | 0 | 0 |
| 4 | 10 | 8 | 320 | 16 | 15 | 1800 | 20 | 18 | 3240 | 22 | 19 | 3971 |
| 5 | 14 | 12 | 1008 | 18 | 15 | 2025 | 17 | 15 | 1912.5 | 16 | 12 | 1152 |
| 6 | 0 | 0 | 0 | 8 | 8 | 256 | 14 | 11 | 847 | 0 | 0 | 0 |
| 7 | 0 | 0 | 0 | 7 | 3 | 31.5 | 3 | 3 | 13.5 | 25 | 23 | 6612.5 |
| 8 | 12 | 11 | 726 | 3 | 3 | 13.5 | 7 | 5 | 87.5 | 25 | 20 | 5000 |
| 9 | 0 | 0 | 0 | 15 | 15 | 1687.5 | 0 | 0 | 0 | 12 | 10 | 600 |
| 10 | 10 | 7 | 245 | 0 | 0 | 0 | 20 | 19 | 3610 | — | — | — |
| Average | | | 499 ± 202 | | | 1102 ± 344 | | | 1473 ± 457 | | | 2417 ± 844 |

TABLE 2

Tumor (Ehrlich's Carcinoma) Growth Dynamics in White Mice (Product 1)

| Animal No. | 13th day | | | 16th day | | | 20th day | | | 23rd day | | |
|---|---|---|---|---|---|---|---|---|---|---|---|---|
| | a | b | V, mm³ | a | b | V, mm³ | a | b | V, mm³ | a | b | V, mm³ |
| 1 | 6 | 5 | 75 | 11 | 9 | 445.5 | 11 | 9 | 445.5 | 10 | 8 | 320 |
| 2 | 12 | 10 | 600 | 3 | 3 | 13.5 | 17 | 14 | 1666 | 18 | 14 | 1764 |
| 3 | 12 | 9 | 486 | 17 | 11 | 1028.5 | 12 | 8 | 384 | 7 | 5 | 87.5 |
| 4 | 6 | 4 | 48 | 11 | 8 | 352 | 21 | 15 | 2362.5 | 23 | 21 | 5071.5 |
| 5 | 6 | 3 | 27 | 7 | 5 | 87.5 | 21 | 10 | 1050 | 16 | 16 | 2048 |
| 6 | 0 | 0 | 0 | 18 | 16 | 2304 | 13 | 11 | 786.5 | 7 | 5 | 87.5 |
| 7 | 8 | 6 | 144 | 11 | 6 | 198 | 0 | 0 | 0 | 14 | 13 | 1183 |
| 8 | 17 | 14 | 1666 | 0 | 0 | 0 | 15 | 12 | 1080 | 21 | 16 | 2688 |
| 9 | 11 | 8 | 352 | 19 | 15 | 2137.5 | — | — | — | — | — | — |
| Average | | | 378 ± 176 | | | 730 ± 301 | | | 972 ± 268 | | | 1656 ± 565 |

TABLE 3

Tumor (Ehrlich's Carcinoma) Growth Dynamics in White Mice (Product 2)

| Animal No. | 13th day | | | 16th day | | | 20th day | | | 23rd day | | |
|---|---|---|---|---|---|---|---|---|---|---|---|---|
| | a | b | V, mm³ | a | b | V, mm³ | a | b | V, mm³ | a | b | V, mm³ |
| 1 | 0 | 0 | 0 | 5 | 3 | 22.5 | 10 | 8 | 320 | 17 | 15 | 1912.5 |
| 2 | 7 | 5 | 87.5 | 7 | 4 | 56 | 9 | 8 | 288 | 12 | 10 | 600 |
| 3 | 8 | 6 | 144 | 3 | 3 | 13.5 | 9 | 7 | 220.5 | 11 | 9 | 445.5 |
| 4 | 4 | 3 | 18 | 8 | 7 | 196 | 4 | 3 | 18 | 4 | 3 | 18 |
| 5 | 7 | 7 | 171.5 | 11 | 8 | 352 | 5 | 4 | 40 | 0 | 0 | 0 |
| 6 | 9 | 8 | 288 | 12 | 10 | 600 | 0 | 0 | 0 | 10 | 8 | 320 |
| 7 | 0 | 0 | 0 | 11 | 9 | 445.5 | 11 | 9 | 445.5 | 15 | 13 | 1267.5 |
| 8 | 14 | 12 | 1008 | 11 | 7 | 269.5 | 13 | 11 | 786.5 | 10 | 10 | 500 |
| 9 | 4 | 4 | 32 | 0 | 0 | 0 | 14 | 11 | 847 | — | — | — |
| Average | | | 194 ± 107 | | | 217 ± 72 | | | 330 ± 105 | | | 633 ± 230 |

FIG. 1 shows the growth dynamics of an inoculated Ehrlich's carcinoma in white mice under treatment with the chemical products. As such, Products No. 1 (Cisplatin) and No. 2 exhibit antitumor properties. The product based on Composition No. 2, where a complex compound of divalent platinum with alloferon oligopeptide is used as an active ingredient, was found to be substantially (three times) more efficient than Cisplatin.

The invention claimed is:

1. An anti-tumor agent composition consisting of:
0.05 to 0.1% wt of alloferon;
0.01 to 0.05% wt of cis-diamminedichloridoplatinum;
in a 0.9% sodium chloride solution.

* * * * *